United States Patent [19]
Berg et al.

[11] Patent Number: 5,147,512
[45] Date of Patent: Sep. 15, 1992

[54] SEPARATION OF KETONE ISOMERS BY EXTRACTIVE DISTILLATION

[75] Inventors: Lloyd Berg, 1314 S. Third Ave., Bozeman, Mont. 59715; Thomas A. Edison, Bozeman, Mont.

[73] Assignee: Lloyd Berg, Bozeman, Mont.

[21] Appl. No.: 723,043

[22] Filed: Jun. 28, 1991

[51] Int. Cl.$^5$ .................... B01D 3/40; C07C 45/83
[52] U.S. Cl. ........................... 203/51; 203/57; 203/58; 203/60; 203/62; 203/63; 203/64; 568/410
[58] Field of Search ............... 203/51, 64, 57, 58, 203/62, 63, 60; 568/410

[56] References Cited

U.S. PATENT DOCUMENTS

| | | | |
|---|---|---|---|
| 2,010,384 | 8/1935 | Van Melsen et al. | 568/410 |
| 2,245,945 | 6/1941 | Van Dijck et al. | 568/410 |
| 2,288,281 | 6/1942 | Huijser et al. | 568/410 |
| 3,493,618 | 2/1970 | Fuhrmann | 568/410 |
| 4,793,901 | 12/1988 | Berg et al. | 203/51 |

*Primary Examiner*—Wilbur Bascomb, Jr.

[57] ABSTRACT

The higher boiling ketone isomers are difficult to separate one from another by conventional distillation or rectification because of the close proximity of their boiling points. Ketone isomers can be readily separated from each other by extractive distillation. Typical examples of effective agents are: for 3-pentanone from 2-pentanone, dipropylene glycol; 3-hexanone from 2-hexanone, butoxypropanol; 3-heptanone from 2-heptanone, 50% ethylene glycol—50% butoxypropanol; 3-octanone from 2-octanone, ethylene glycol diacetate.

4 Claims, No Drawings

SEPARATION OF KETONE ISOMERS BY EXTRACTIVE DISTILLATION

FIELD OF THE INVENTION

This invention relates to a method for separating ketone isomers one from another using certain higher boiling liquids as the agent in extractive distillation.

DESCRIPTION OF PRIOR ART

Extractive distillation is the method of separating close boiling compounds from each other by carrying out the distillation in a multiple rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling compound. This usually requires that the extractive agent boil twenty Centrigrade degrees or more above the lowest boiling component.

At the bottom of a continuous column, the less volatile components of the close boiling mixture and the extractive agent are continuously removed from the column. The usual methods of separation of these two components are the use of another rectification column, cooling and phase separation or solvent extraction.

Extractive distillation typically requires the addition of an equal amount to twice as much extractive agent as the ketone isomer mixture on each plate of the rectification column. The extractive agent should be heated to about the same temperature as the plate into which it is introduced. Thus extractive distillation imposes an additional heat requirement on the column as well as somewhat larger plates. However this is less than the increase caused by the additional agents requires if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with the extracted ketone otherwise it will form a two-phase azeotrope with the extracted ketone in the recovery column and some other method of separation will have to be employed.

In the manufacture of the higher ketones, the process frequently yields a mixture of isomers. Depending upon the number of isomers and the difference in their molecular structure, the boiling points of some isomers can be very close together. The closest boilers in a series of isomeric ketones are listed as follows for their boiling points and relative volatilities: 2-pentanone, B.P.=100° C., 3-pentanone, B.F.=102° C., rel. vol.=1.02; 3-hexanone, B.P.=123° C., 2-hexanone, B.P.=127° C., rel. vol.=1.15; 3-heptanone, B.P.=146° C., 2-heptanone, B.P.+146° C., rel. vol.=1.17; 3-octanone, B.P.=168° C., 2-octanone, B.P.=173° C., rel. vol.=1.15.

TABLE 1

| Plates Required To Effect Separation Of 99% Purity | | |
|---|---|---|
| Relative Volatility | Theoretical Plates | Actual Plates, 75% Efficiency |
| 1.02 | 465 | 620 |
| 1.15 | 66 | 88 |
| 1.17 | 59 | 79 |
| 1.25 | 41 | 55 |
| 1.30 | 35 | 47 |
| 1.35 | 31 | 41 |
| 1.40 | 27 | 36 |

Table 1 shows that to separate a mixture having a relative volatility of 1.15, 66 theoretical or 88 actual plates would be required to separate in 99% purity. If the relative volatility could be improved to 1.3, only 47 actual plates would be required and with a relative volatility of 1.4, only 36 actual plates are needed.

Extractive distillation would be an attractive method of effecting the separation of ketone isomers one from another, if agents can be found that (1) will increase the relative volatility of one isomer to the other and (2) are easy to recover from the ketone being extracted, that is, form no azeotrope with ketone and boil sufficiently above it to make separation by rectification possible with only a few plates.

Pacoud & Dallemagne, U.S. Pat. No. 3,013,954 described the use of an auxiliary substance to separate the ketone acetone from acetic acid, formic acid, formaldehyde and water. The auxiliary substance used was isopropyl ether.

Carpenter, Taylor & McNair, U.S. Pat. No. 3,228,985 described the use of aqueous sodium carbonate in a solvent extraction process to recover methyl ethyl ketone from a complex mixture of water, acids, alcohols, ketone and esters. Van Melsen & Langedijk, U.S. Pat. No. 2,010,384 described a process for separating isomeric pentanones using a water soluble bisulfite as the agent in a solvent extraction method.

OBJECTIVE OF THE INVENTION

The object of this invention is to provide a process or method of extractive distillation that will enhance the relative volatility of ketone isomers one from another in their separation in a rectification column. It is a further object of this invention to identify organic compounds which in addition to the above constraints, are stable, can be separated from the ketone being extracted by rectification with relatively few plates and can be recycled to the extractive distillation column and reused with little decomposition.

SUMMARY OF THE INVENTION

The objects of the invention are provided by a process for separating ketone isomers one from another which entails the use of certain glycols, either alone or admixed with certain high boiling organic compounds in an extractive distillation.

DETAILED DESCRIPTION OF THE INVENTION

3-Pentanone From 2-Pentanone:

We have discovered that certain glycols, either alone or admixed with certain high boiling organic compounds will effectively enhance the relative volatility of 3-pentanone to 2-pentanone by rectification when employed as the agent in extractive distillation. Table 2 lists the glycols and certain high boiling organic compounds that we have found to be effective.

The glycols and mixtures which are effective in the separation of 3-pentanone from 2-pentanone are propylene glycol, 1,3-butanediol, 1,2-butanediol, triethylene glycol, tetraethylene glycol, dipropylene glycol, hexylene glycol, 1,4-butanediol, polyethylene glycol 200, 2-methyl-1,3-propanediol, 50% ethylene glycol, 50% propoxypropanol, 67% ethylene glycol, 33% dipropylene glycol and 67% ethylene glycol, 33% polyethylene glycol 200.

Three compounds, namely triethylene glycol, 1,4-butanediol and dipropylene glycol, whose relative volatility had been determined in a vapor-liquid equilibrium still and reported in Table 2, were then evaluated in a glass perforated plate rectification column possessing 7.3 theoretical plates. The results are listed in Table 4 and show that triethylene glycol gave a relative volatility of 1.167, 1,4-butanediol gave 1.25 and dipropylene gave 1.63.

Table 3 lists several glycols that might have been expected to be effective but which were not.

TABLE 2

Effective Agents For Separating 3-Pentanone From 2-Pentanone

| Compounds | Relative Volatility |
| --- | --- |
| None | 1.02 |
| 50% Ethylene glycol, 50% Propoxypropanol | 1.14 |
| Propylene glycol | 1.18 |
| 1,3-Butanediol | 1.31 |
| 1,2-Butanediol | 1.29 |
| Triethylene glycol | 1.22 |
| tetraethylene glycol | 1.19 |
| Dipropylene glycol | 1.30 |
| hexylene glycol | 1.15 |
| 1,4-Butanediol | 1.25 |
| Polyethylene glycol 200 | 1.30 |
| 67% Ethylene glycol, 33% Dipropylene glycol | 1.17 |
| 67% Ethylene glycol, 33% polyethylene glycol 200 | 1.30 |
| 2-Methyl-1,3-propanediol | 1.30 |

TABLE 3

Ineffective Agents For Separating 3-Pentanone From 2-Pentanone

| Compounds | Relative Volatility |
| --- | --- |
| 1,5-Pentanediol | 1.02 |
| 1,6-Hexanediol | 1.08 |
| Diethylene glycol | 1.06 |
| Tripropylene glycol | 1.03 |
| Polyethylene glycol 300 | 1.04 |

TABLE 4

Data From Runs Made in Rectification Column - 3-Pentanone From 2-Pentanone

| Agent | Column | Time hrs. | Weight % 3-Pentanone | Weight % 2-Pentanone | Relative Volatility |
| --- | --- | --- | --- | --- | --- |
| Triethylene glycol | Overhead | 1.5 | 58.7 | 41.3 | 1.167 |
| | Bottoms | | 31.4 | 68.6 | |
| 1,4-Butanediol | Overhead | 2 | 72.1 | 27.9 | 1.25 |
| | Bottoms | | 33.5 | 66.5 | |
| Dipropylene glycol | Overhead | 1 | 98.7 | 1.3 | 1.63 |
| | Bottoms | | 67.3 | 32.7 | |

3-Hexanone From 2-Hexanone:

We have discovered that certain oxygenated organic compounds will effectively enhance the relative volatility of 3-hexanone to 2-hexanone when employed as the agent in extractive distillation. Table 5 lists the compounds that we have found to be effective. The relative volatilities shown in Table 5 were obtained in an Othmer type vapor-liquid equilibrium still. The compounds and mixture which are effective in the separation of 3-hexanone from 2-hexanone are triethylene glycol, dipropylene glycol methyl ether, n-octanol, ethylene glycol diacetate, diethylene glycol hexyl ether, benzyl alcohol, tripropylene glycol methyl ether, butoxypropanol, propoxypropanol, sulfolane, benzonotrile and 50% ethylene glycol—50% butoxypropanol.

TABLE 5

Effective Agents For Separating 3-Hexanone From 2-Hexanone

| Compounds | Relative Volatility |
| --- | --- |
| None | 1.15 |
| Ethylene glycol, Butoxypropanol | 1.27 |
| Triethylene glycol | 1.22 |
| Dipropylene glycol methyl ether | 1.25 |
| Ethylene glycol diacetate | 1.20 |
| Diethylene glycol hexyl ether | 1.23 |
| n-Octanol | 1.23 |
| Tripropylene glycol methyl ether | 1.27 |
| Butoxypropanol | 1.28 |
| Propoxypropanol | 1.33 |
| Sulfolane | 1.22 |
| Benzyl alcohol | 1.23 |
| Benzonitrile | 1.28 |

TABLE 6

Ineffective Agents For Separating 3-Hexanone From 2-Hexanone

| Compounds | Relative Volatility |
| --- | --- |
| Propylene glycol | 1.16 |
| Ethylene glycol hexyl ether | 1.10 |
| Diethylene glycol methyl ether | 1.16 |
| Glycerol triacetate | 1.19 |
| Diethylene glycol butyl ether | 1.19 |
| Isononyl alcohol | 1.17 |
| Dodecanol | 1.18 |
| Nitrobenzene | 1.13 |
| 2-Nitrotoluene | 1.01 |
| 3-Nitrotoluene | 1.14 |
| 2-Methylpyrrolidone | 1.13 |
| o-tert. Butyl phenol | 1.12 |
| Phenol | 1.19 |
| Ethyl acetoacetate | 1.17 |

TABLE 7

Data From Run Made In Rectification Column - 3-Hexanone From 2-Hexanone

| Agent | Column | Time hrs. | Weight % 3-Hexanone | Weight % 2-Hexanone | Relative Volatility |
| --- | --- | --- | --- | --- | --- |
| Butoxypropanol | Overhead | 1 | 71.5 | 28.5 | 1.32 |
| | Bottoms | | 25.8 | 74.2 | |
| Butoxypropanol | Overhead | 2 | 70.2 | 29.8 | 1.31 |
| | Bottoms | | 24.4 | 75.6 | |

Table 6 lists several compounds that might have been expected to be effective but which were not.

One compound, butoxypropanol, whose relative volatility had been determined in the vapor-liquid equilibrium still and reported in Table 5, was then evaluated in a glass perforated plate rectification column possessing 7.3 theoretical plates. The results are listed in Table 7 and show that butoxypropanol gave a relative volatility of 1.31.

3-Heptanone From 2-Heptanone:

We have discovered that certain oxygenated organic compounds will effectively enhance the relative volatility of 3-heptanone to 2-heptanone when employed as the agent in extractive distillation. Table 8 lists the compounds that we have found to be effective. The relative volatilities shown in Table 8 were obtained in an Othmer type vapor-liquid equilibrium still. The compounds and mixtures which are effective in the separation of 3-heptanone from 2-heptanone are propylene glycol, triethylene glycol, hexylene glycol, 1,2-butanediol ethylene glycol-butoxypropanol, diethylene glycol-butoxypropanol, propylene glycol-butoxypropanol, 1,4-butanediol-butoxypropanol and nitrobenzene-butoxypropanol. Table 9 lists several compounds and mixtures that might have been expected to be effective but which were not. One mixture, 50% ethylene glycol, 50% butoxypropanol, whose relative volatility had been determined in the vapor-liquid equilibrium still and reported in Table 8, was then evaluated in a glass perforated plate rectification column possessing 7.3 theoretical plates. The results are listed in Table 10 and show that 50% ethylene glycol—50% butoxypropanol gave a relative volatility of 1.28.

3-Octanone From 2-Octanone:

We have discovered that certain oxygenated organic compounds will effectively enhance the relative volatility of 3-octanone to 2-octanone when employed as the agent in extractive distillation. Table 11 lists the compounds and mixtures that we have found to be effective. The relative volatilities shown in Table 11 were obtained in an Othmer type vapor-liquid equilibrium still. The compounds and mixtures which are effective are ethylene carbonate, propylene carbonate, sulfolane, 2-hydroxyacetophenone, tripropylene glycol methyl ether, ethylene glycol hexyl ether, ethylene glycol diacetate, dipropylene glycol methyl ether, benzonitrole, n-(2-hydroxyethyl-2-pyrrolidone), butoxyethoxy-2-propanol, diethylene glycol hexyl ether, triethylene glycol-diethylene glycol butyl ether and polyethylene glycol 200—tripropylene glycol methyl ether.

TABLE 8

Effective Agents For Separating 3-Heptanone From 2-Heptanone

| Compounds | Relative Volatility |
|---|---|
| None | 1.17 |
| Propylene glycol | 1.29 |
| Triethylene glycol | 1.28 |
| Hexylene glycol | 1.23 |
| 1,2-Butanediol | 1.24 |
| Ethylene glycol, Butoxypropanol | 1.28 |
| Diethylene glycol, Butoxypropanol | 1.26 |
| Propylene glycol, Butoxypropanol | 1.25 |
| 1,4-Butanediol, Butoxypropanol | 1.27 |
| Nitrobenzene, Butoxypropanol | 1.28 |

TABLE 9

Ineffective Agents For Separating 3-Heptanone From 2-Heptanone

| Compounds | Relative Volatility |
|---|---|
| Dimethylsulfoxide | 1.18 |
| Dimethylacetamide | 1.10 |
| Adiponitrile | 1.12 |
| 1,2-Butanediol, Butoxypropanol | 1.16 |
| 1,3-Butanediol, Butoxypropanol | 1.10 |
| 1,5-Pentanediol, Butoxypropanol | 1.12 |
| 1,6-Hexanediol | 1.20 |
| Dipropylene glycol | 1.05 |
| Tripropylene glycol | 1.19 |
| Polyethylene glycol 200 | 1.21 |
| Polyethylene glycol 300 | 1.18 |
| Butoxypropanol | 1.14 |
| Tetraethylene glycol | 1.18 |
| 2-Methoxymethyl ether | 1.00 |
| 2-Nitrotoluene, Butoxypropanol | 1.18 |
| 3-Nitrotoluene | 1.15 |
| 4-Nitrotoluene | 1.13 |

TABLE 10

Data From Run Made In Rectification Column - 3-Heptanone From 2-Heptanone

| Agent | Column | time hrs. | Weight % 3-Heptanone | Weight % 2-Heptanone | Relative Volatility |
|---|---|---|---|---|---|
| 50% Ethylene glycol, 50% Butoxypropanol | Overhead Bottoms | 1 | 74 33.9 | 26 66.1 | 1.262 |
| 50% Ethylene glycol, 50% Butoxypropanol | Overhead Bottoms | 1.7 | 73.8 32 | 26.2 68 | 1.28 |

TABLE 11

Effective Agents For Separating 3-Octanone From 2-Octanone

| Compounds | Relative Volatility |
|---|---|
| None | 1.15 |
| Ethylene carbonate | 1.25 |
| Propylene carbonate | 1.23 |
| 2-Hydroxyacetophenone | 1.22 |
| Sulfolane | 1.23 |
| Tripropylene glycol methyl ether | 1.25 |
| Ethylene glycol hexyl ether | 1.24 |
| Ethylene glycol diacetate | 1.28 |
| Dipropylene glycol methyl ether | 1.21 |
| Benzonitrile | 1.20 |
| N-(2-Hydroxyethyl-2-Pyrrolidone) | 1.21 |
| Triethylene glycol, Diethylene glycol butyl ether | 1.20 |
| Polyethylene glycol 200, Tripropylene glycol methyl ether | 1.23 |
| Butoxyethoxy-2-propanol | 1.24 |
| Diethylene glycol hexyl ether | 1.28 |

TABLE 12

Ineffective Agents For Separating 3-Octanone From 2-Octanone

| Compounds | Relative Volatility |
|---|---|
| Adiponitrile | 1.14 |
| Butyl benzoate | 1.11 |
| Dihexyl phthalate | 1.03 |
| Methyl salicylate | 1.09 |
| Pelargonic acid | 1.16 |
| Polyethylene glycol 200 | 1.19 |
| Polyethylene glycol 300 | 1.15 |
| Diethylene glycol butyl ether | 1.18 |
| Glycerol triacetate | 1.08 |
| Diethylene glycol diethyl ether | 1.06 |
| Ethyl acetoacetate | 1.15 |
| Diethylene glycol methyl ether | 1.14 |
| Diethyl malonate | 1.10 |

TABLE 12-continued

Ineffective Agents For Separating 3-Octanone From 2-Octanone

| Compounds | Relative Volatility |
| --- | --- |
| Triisononyl trimellitate | 1.13 |
| N-Methyl-2-pyrrolidone | 1.16 |
| N-Cyclohexyl-2-pyrrolidone | 1.02 |
| Diisononyl adipate | 1.19 |
| Tridecyl phthalate | 1.10 |
| Tributyl phosphate | 1.16 |
| Tri-2-Ethyl hexyl trimellitate | 1.09 |
| Ethylene glycol phenyl ether | 1.19 |
| 2-Ethyl hexyl acetate | 1.17 |
| Diisodecyl phthalate | 1.15 |
| Tetraethylene glycol, Tripropylene glycol methyl ether | 1.16 |
| Propylene carbonate, n-Methyl-2-pyrrolidone | 1.13 |

TABLE 13

Data From Runs Made In Rectification Column - 3-Octanone From 2-Octanone

| Agent | Column | Time hrs. | Weight % 3-Octanone | Weight % 2-Octanone | Relative Volatility |
| --- | --- | --- | --- | --- | --- |
| Dipropylene glycol methyl ether | Overhead | 2 | 38.6 | 61.4 | 1.20 |
| Dipropylene glycol methyl ether | Bottoms | | 14.1 | 85.9 | |
| Dipropylene glycol methyl ether | Overhead | 3 | 39.6 | 60.4 | 1.21 |
| Dipropylene glycol methyl ether | Bottoms | | 14.4 | 85.6 | |
| Ethylene glycol diacetate | Overhead | 1 | 54.4 | 45.6 | 1.36 |
| Ethylene glycol diacetate | Bottoms | | 11.1 | 88.9 | |
| Ethylene glycol diacetate | Overhead | 2 | 57.6 | 42.4 | 1.39 |
| Ethylene glycol diacetate | Bottoms | | 10.7 | 89.3 | |

Table 12 lists several compounds and mixtures that might have been expected to be effective but which were not.

Two compounds, dipropylene glycol methyl ether and ethylene glycol diacetate, whose relative volatilities had been determined in the vapor-liquid equilibrium still and reported in Table 11, were then evaluated in a glass perforated plate rectification column possessing 7.3 theoretical plates. The results are listed in Table 13 and show that dipropylene glycol methyl ether gave a relative volatility of 1.21 and ethylene glycol diacetate gave a relative volatility of 1.39.

THE USEFULNESS OF THE INVENTION

The usefulness or utility of this invention can be demonstrated by referring to the data presented in Tables 1-13. All of the successful extractive agents show that ketone isomers can be separated one from another by means of distillation in a rectification column and that the ease of separation as measured by relative volatility is considerable. Without these extractive distillation agents, only slight improvement will occur in a rectification column. The data also show that the most attractive agents will operate at a boilup rate low enough to make this a useful and efficient method of recovering high purity ketone from any mixture of ketone isomers. The stability of the compounds used and the boiling point difference is such that complete recovery and recycle is obtainable by a simple distillation and the amount required for make-up is small.

WORKING EXAMPLES

EXAMPLE 1

Ten grams of 3-pentanone, 40 grams of 2-pentanone and 20 grams of 1,3-butanediol were charged to an Othmer type vapor-liquid still and refluxed for six hours. Analysis by gas chromatography gave a vapor composition of 19.2% 3-pentanone, 80.8% 2-pentanone; a liquid composition of 15.4% 3-pentanone, 84.6% 2-pentanone which is a relative volatility of 1.31.

EXAMPLE 2

A glass perforated plate rectification column was calibrated with m-xylene and o-xylene which possesses a relative volatility of 1.11 and found to have 7.3 theoretical plates. A solution comprising 250 grams 3-pentanone and 50 grams of 2-pentanone was placed in the stillpot and heated. When refluxing began, an extractive agent comprising dipropylene glycol was pumped into the column at a rate of 15 ml/min. The boil-up rate was 20 ml/min. and the temperature of the extractive agent as it entered the column was 85° C. After establishing the feed rate of the extractive agent, the heat input to the m-xylene and o-xylene in the stillpot was adjusted to give a total reflux rate of 30–40 ml/min. After one hour of operation, the overhead and bottoms samples of approximately two ml. were collected and analysed by gas chromatography. The overhead analysis was 98.7% 3-pentanone, 1.3% 2-pentanone. The bottoms analysis was 67.3% 3-pentanone, 32.7% 2-pentanone. Using these compositions in the Fenske equation with the number of theoretical plates in the column being 7.3, gave an average relative volatility of 1.63. for each theoretical plate. This run is presented in Table 4.

EXAMPLE 3

Ten grams of 3-hexanone, 30 grams of 2-hexanone and 20 grams of tripropylene glycol methyl ether were charged to an Othmer type vapor-liquid equilibrium still and refluxed for 12 hours. Analysis by gas chromatography gave a vapor composition of 21.25 3-hexanone, 78.8% 2-hexanone; a liquid composition of 17.4% 3-hexanone, 82.6% 2-hexanone which is a relative volatility of 1.27.

EXAMPLE 4

A glass perforated plate rectification column was calibrated with m-xylene and o-xylene which possesses a relative volatility of 1.11 and found to have 7.3 theoretical plates. A solution comprising 200 grams of 3-hexanone and 100 grams of 2-hexanone was placed in the stillpot and heated. When refluxing began, an extractive agent comprising butoxypropanol was pumped into the column at a rate of 15 ml/min. The boil-up rate was 20 ml/min. and the temperature of the extractive agent as it entered the column was 85° C. After establishing the feed rate of the extractive agent, the heat input to the m-xylene and o-xylene in the stillpot was adjusted to give a total reflux rate of 30–40 ml/min. After one hour of operation, the overhead and bottoms samples of approximately two ml. were collected and analysed by gas chromatography. The overhead analysis was 71.5% 3-hexanone, 28.5% 2-hexanone. The bottoms analysis was 25.8% 3-hexanone, 74.2% 2-hexanone. Using these compositions in the Fenske equation with the number of theoretical plates in the column being 7.3, gave an average relative volatility of 1.32 for each theoretical plate. This run is presented in Table 7.

EXAMPLE 5

Ten grams of 3-heptanone, 30 grams of 2-heptanone and 20 grams of triethylene glycol were charged to an Othmer type vapor-liquid equilibrium still and refluxed for five hours. Analysis by gas chromatography gave a vapor composition of 18.4% 3-heptanone, 81.6% 2-heptanone; a liquid composition of 15% 3-heptanone, 85% 2-heptanone which is a relative volatility of 1.28.

EXAMPLE 6

A glass perforated plate rectification column was calibrated with m-xylene and o-xylene which possesses a relative volatility of 1.11 and found to have 7.3 theoretical plates. A solution comprising 100 grams of 3-heptanone and 200 grams of 2-heptanone was placed in the stillpot and heated. When refluxing began, an extractive agent comprising 50% ethylene glycol, 50% butoxypropanol was pumped into the column at a rate of 15 ml/min. The boil-up rate was 20 ml/min. and the temperature of the extractive agent as it entered the column was 85° C. After establishing the feed rate of the extractive agent, the heat input to the m-xylene and o-xylene in the stillpot was adjusted to give a total reflux rate of 30-40 ml/min. After one hour of operation, the overhead and bottoms samples of approximately two ml. were collected and analysed by gas chromatography. The overhead analysis was 74% 3-heptanone, 26% 2-heptanone. The bottoms analysis was 33.9% 3-heptanone, 66.1% 2-heptanone. Using these compositions in the Fenske equation with the number of theoretical plates in the column being 7.3, gave an average relative volatility of 1.26 for each theoretical plate. This run is presented in Table 10.

EXAMPLE 7

Ten grams of 3-octanone, 30 grams of 2-octanone and 20 grams of diethylene glycol hexyl ether were charged to an Othmer type vapor-liquid equilibrium still and refluxed for four hours. Analysis by gas chromatography gave a vapor composition of 13.15 3-octanone, 86.9% 2-octanone; a liquid composition of 10.5% 3-octanone, 89.5% 2-octanone which is a relative volatility of 1.28.

EXAMPLE 8

A glass perforated plate rectification column was calibrated with m-xylene and o-xylene which possesses a relative volatility of 1.11 and found to have 7.3 theoretical plates. A solution comprising 50 grams of 3-octanone and 250 grams of 2-octanone was placed in the stillpot and heated. When refluxing began, an extractive agent comprising ethylene glycol diacetate was pumped into the column at a rate of 15 ml/min. The boil-up rate was 20 ml/min. and the temperature of the extractive agent as it entered the column was 85° C. After establishing the feed rate of the extractive agent, the heat input to the m-xylene and o-xylene in the stillpot was adjusted to give a total reflux rate of 30-40 ml/min. After two hour of operation, the overhead and bottoms samples of approximately two ml. were collected and analysed by gas chromatography. The overhead analysis was 57.6% 3-octanone, 42.4% 2-octanone. The bottoms analysis was 10.7% 3-octanone, 89.3% 2-octanone. Using these compositions in the Fenske equation with the number of theoretical plates in the column being 7.3, gave an average relative volatility of 1.39 for each theoretical plate. This run is presented in Table 13.

We claim:

1. A method for recovering 3-pentanone from a mixture of 3-pentanone and 2-pentanone in the presence of about one part of an extractive agent per part of 3-pentanone-2-pentanone mixture, recovering 3-pentanone as overhead product and obtaining the 2-pentanone and the extractive agent from the stillpot, wherein said extractive agent comprises at least one material selected from the group consisting of ethylene glycol, propylene glycol, 1,3-butanediol, 1,2-butanediol, triethylene glycol, tetraethylene glycol, dipropylene glycol, hexylene glycol, 1,4-butanediol, polyethylene glycol, 2-methyl-1,3-propanediol and propoxypropanol.

2. A method for recovering 3-hexanone from a mixture of 3-hexanone and 2-hexanone which comprises distilling a mixture of 3-hexanone and 2-hexanone in the presence of about one part of an extractive agent per part of 3-hexanone-2-hexanone mixture, recovering 3-hexanone as overhead product and obtaining the 2-hexanone and the extractive agent from the stillpot, wherein said extractive agent comprising at least one material selected from the group consisting of ethylene glycol, triethylene glycol, dipropylene glycol methyl ether, n-octanol, ethylene glycol diacetate, diethylene glycol hexyl ether, benzyl alcohol, tripropylene glycol methyl ether, butoxypropanol, sulfolane, propoxypropanol and benzonitrile.

3. A method for recovering 3-heptanone from a mixture of 3-heptanone and 2-heptanone which comprises distilling a mixture of 3-heptanone and 2-heptanone in the presence of about one part of an extractive agent per part of 3-heptanone-2-heptanone mixture, recovering 3-heptanone as overhead product and obtaining the 2-heptanone and the extractive agent from the stillpot, wherein said extractive agent comprises at least one material selected from the group consisting of ethylene glycol, propylene glycol, triethylene glycol, hexylene glycol, diethylene glycol, 1,2-butanediol, 1,4-butanediol, butoxypropanol and nitrobenzene.

4. A method for recovering 3-octanone from a mixture of 3-octanone and 2-octanone which comprises distilling a mixture of 3-octanone and 2-octanone in the presence of about one part of an extractive agent per part of 3-octanone-2-octanone mixture, recovering 3-octanone as overhead product and obtaining the 2-octanone and the extractive agent from the stillpot, wherein said extractive agent comprises at least one material selected from the group consisting of ethylene carbonate, propylene carbonate, sulfolane, 2-hydroxyacetophenone, tripropylene glycol methyl ether, ethylene glycol hexyl ether, ethylene glycol diacetate, dipropylene glycol methyl ether, N-(2-hydroxyethyl-2-pyrrolidone), butoxyethoxy-2-propanol, diethylene glycol hexyl ether, triethylene glycol, diethylene glycol butyl ether and polyethylene glycol.

* * * * *